United States Patent
Rosenberg

[11] Patent Number: 6,048,203
[45] Date of Patent: Apr. 11, 2000

[54] METHOD AND DEVICE FOR FORMING AND ATTACHING A NON-METAL DENTAL PROSTHESIS

[76] Inventor: Jeffrey M Rosenberg, 413 Bainbridge St., Philadelphia, Pa. 19147

[21] Appl. No.: 09/092,822
[22] Filed: Jun. 8, 1998
[51] Int. Cl.[7] .................................................. A61C 8/00
[52] U.S. Cl. ...................... 433/173; 433/172; 433/201.1
[58] Field of Search ................................... 433/172, 173, 433/174, 201.1

[56] References Cited

U.S. PATENT DOCUMENTS

| | | | |
|---|---|---|---|
| 3,849,887 | 11/1974 | Brainin | 433/173 |
| 4,281,991 | 8/1981 | Michl | 433/202 |
| 4,713,006 | 12/1987 | Hakamatsuka et al. | 433/173 |
| 4,867,683 | 9/1989 | Meisel | 433/181 |
| 4,894,012 | 1/1990 | Goldberg | 433/215 |
| 5,125,839 | 6/1992 | Ingber et al. | 433/173 |
| 5,171,147 | 12/1992 | Burgess | 433/180 |
| 5,176,951 | 1/1993 | Rudo | 428/229 |
| 5,413,480 | 5/1995 | Musikant et al. | 433/173 |
| 5,429,505 | 7/1995 | Fortin | 433/172 |
| 5,439,380 | 8/1995 | Marlin | 433/172 |
| 5,556,280 | 9/1996 | Pelak | 433/172 |
| 5,662,474 | 9/1997 | Jorneus | 433/172 |

*Primary Examiner*—John J. Wilson
*Attorney, Agent, or Firm*—LaMorte & Associates

[57] ABSTRACT

A system and method for filling a dental occlusion with a metal free prosthesis. The method begins by surgically implanting at least one dental implant fixture within the mouth in the area of the occlusion. Once the implant fixture is healed, an abutment is added to each dental implant fixture. An impression of the area of the occlusion is taken directly over any abutment. The impression is used to create a dental model of the area of the occlusion. A metal free prosthesis is fabricated from the model. The metal free prosthesis is then anchored to the abutments.

9 Claims, 4 Drawing Sheets

METHOD AND DEVICE FOR FORMING AND ATTACHING A NON-METAL DENTAL PROSTHESIS

BACKGROUND OF THE INVENTION

1. Field of the Invention

In general, the present invention relates to dental prosthetic devices such as crowns and bridges that attach to the fixture of a dental implant. More particularly, the present invention relates to the method of forming dental prosthetic devices and the method of anchoring such prosthetic devices to the fixture of a dental implant.

2. Description of the Prior Art

In dentistry, the use of dental implants is becoming increasingly popular as a means of anchoring prosthetic devices within the mouth. By using dental implants, prosthetic devices can be anchored directly to bone, as opposed to being anchored to other teeth within the mouth. Accordingly, the stability of the prosthesis does not rely upon the condition of the other teeth within the mouth. Similarly, should the condition of other teeth in the mouth degrade over time, the stability of the prosthesis will remain unaffected.

Dental implants typically include metal fixtures that are surgically inserted into either the bone of the maxillary arch or the bone of the mandibular arch. As the bone grows around the base of the fixture, the fixture becomes firmly set into the bone.

After a fixture has set into the bone and the fixture has healed, an abutment is commonly attached to the fixture. In the prior art, the abutment is a metal structure that is shaped to receive a prosthetic device. The prosthetic device is usually a crown or a bridge that is fabricated using traditional impression modelling techniques. Traditionally, prosthetic devices used in conjunction with dental implants have a metal core upon which porcelain or another laminate structure is applied. The metal core of the prosthetic device is shaped to receive the abutment segment of the implant. As such, a metal-to-metal mechanical interconnection is created between the abutment and the prosthetic device. Such prior art devices and methods are exemplified in U.S. Pat. No. 5,556,280 to Pelak, entitled Method And Apparatus For Appliance Mounting.

Metal-to-metal interconnections between implant abutments and dental prosthetic devices produce very stable and reliable anchoring connections for the prosthetic devices. However, the use of metal does have its disadvantages. If a metal core is used within a prosthetic device, that prosthetic device is opaque. Natural teeth are partially translucent. Accordingly, a prosthetic device with a metal core will never truly have the same appearance as a natural tooth, regardless of its color. Furthermore, in some patients, there can be bio-incompatibility issues when metal is introduced into the mouth. The incompatibility can prevent proper growth of the gums around the base of the prosthetic device.

Recognizing the disadvantages of metal core dental prosthetics, many systems and methods have been developed in the prior art for forming prosthetic dental devices that do not contain metal. Such systems typically utilize fiber reinforced composite materials. In such prior art systems, the fiber reinforced material must be anchored between adjacent teeth because the fiber reinforced material does not bond well to the metal of a dental implant. Furthermore, significant portions of the adjacent teeth must be removed in order to form the structure required to engage the fiber reinforced composite material. Accordingly, the strength of any prosthesis that utilizes fiber reinforced composite material is dependent upon the strength, size and condition of the teeth adjacent to the prosthesis. Furthermore, if any occlusion between teeth is greater than just one or two teeth, such prior art systems cannot be used due to the lack of support available. Prior art systems that utilize fiber reinforced composite material are exemplified by U.S. Pat. No. 4,867,683 to Meisel, entitled Anchoring Device For Dental Prosthesis; U.S. Pat. No. 4,894,012 to Goldberg, entitled Passive Dental Appliances Of Fiber-Reinforced Composites; and U.S. Pat. No. 5,171,147 to Burgess, entitled Dental Bridge.

A need therefore exists for a system and method of forming a metal free prosthetic device that can be attached to the fixture of a dental implant, thereby producing an aesthetically pleasing prosthesis that is anchored directly to bone. This need is met by the present invention system and method as described and claimed below.

SUMMARY OF THE INVENTION

The present invention is a system and method for filling a dental occlusion with a metal free prosthesis. The method begins by surgically implanting at least one dental implant fixture within the mouth in the area of the occlusion. Once the implant fixture is healed, an abutment is added to each dental implant fixture. An impression of the area of the occlusion is taken. The impression can be taken either over the fixtures or directly over any abutment. The impression is used to create a dental model of the area of the occlusion. A metal free prosthesis is fabricated from the model. The metal free prosthesis is then anchored to the abutments.

The prosthesis includes a substructure having a bottom surface, side surfaces and a top surface. The substructure is fabricated from a polymer reinforced glass composite material. Reliefs are disposed on the bottom surface of the substructure that are sized to receive the dental implant abutments. A veneer covers the side surfaces and top surfaces of the substructure, thereby providing the prosthesis with the proper aesthetics.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE INVENTION

Although the present invention system and method can be used to anchor a single tooth prosthesis within the mouth, the present invention system and method are particularly well suited for use in anchoring prosthetic bridge structures within the mouth that contain a plurality of simulated teeth. Accordingly, the illustrated examples of the present invention system will show applications where a prosthetic bridge structure is to be added to the mouth. However, it should be understood that the described system and method can be used to secure a single tooth prosthesis or a prosthesis containing any number of teeth.

Figure 1:
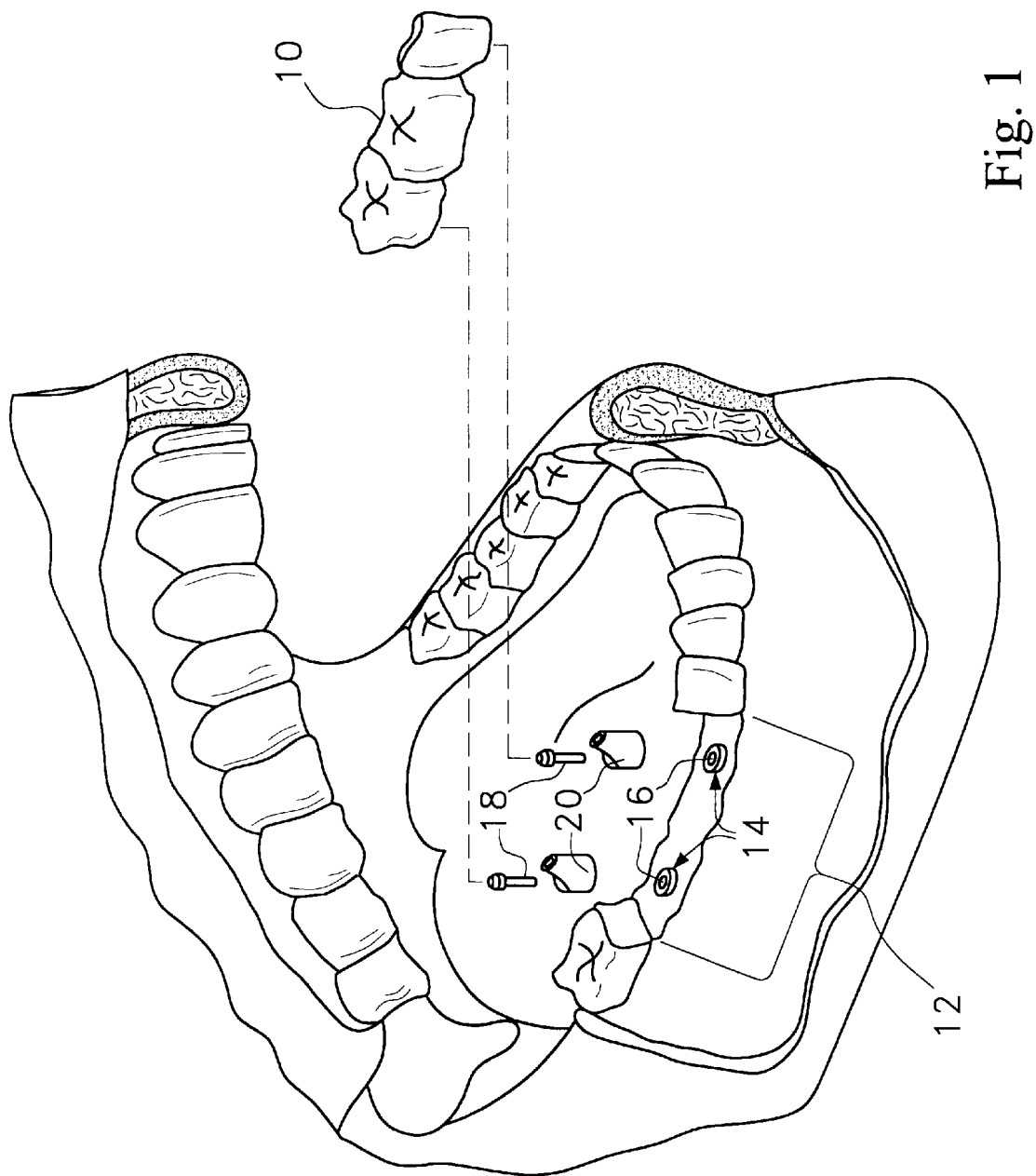
FIG. 1 is an exploded perspective view of one preferred embodiment of the present invention system.

Referring to FIG. 1, a first embodiment of the present invention system is shown. The present invention system is used to create a dental prosthesis 10 and anchor that prosthesis 10 within the mouth. In FIG. 1, a patent's mouth is shown that is in need of a bridge. The patient has an area of occlusion 12 in a common quadrant on the mandibular arch where the first molar and the two premolars are missing. Dental implant fixtures 14 have been surgically embedded in the mandible in the position of the first molar and first premolar. The surgical process of setting dental implants is well known in the field of oral surgery.

In the prior art record, there are many types of dental implants. Most commonly, a dental implant contains a threaded bore in the fixture segment of the implant the extends above the gum. The threaded bore is used to attach abutments to the dental implant fixture. The abutments are used to join the dental prosthetic devices to the implant fixture. Most any such prior art dental implant fixture can be adapted for use in conjunction with the present invention system.

In the shown embodiment, an abutment 20 is provided that attaches to a bore 16 in the dental implant fixture 14 with a mounting screw 18. As will later be more specifically explained, the exterior of the abutment is preferably fabricated from a ceramic optimized polymer. Ceramic optimized polymers are polymer resins mixed with glass-based fillers. Ceramic optimized polymers are commonly used in dentistry as a veneering material. An example of ceramic optimized polymer in the field of dentistry is the Targis™ brand manufactured and sold by Ivoclar Williams of Amherst, N.Y.

The abutments 20 are affixed to the dental implant fixtures 14 with the mounting screws 18. Once the abutments 20 are in place, an impression of the area of the occlusion 12 is taken using standard dental impression modeling techniques. The impression is used to create a model of the area of the occlusion 12 in a dental lab. The model created will include the shape and position of the dental implant fixtures 14 and the abutments 20 that cover the dental implant fixtures 14.

Figure 2:
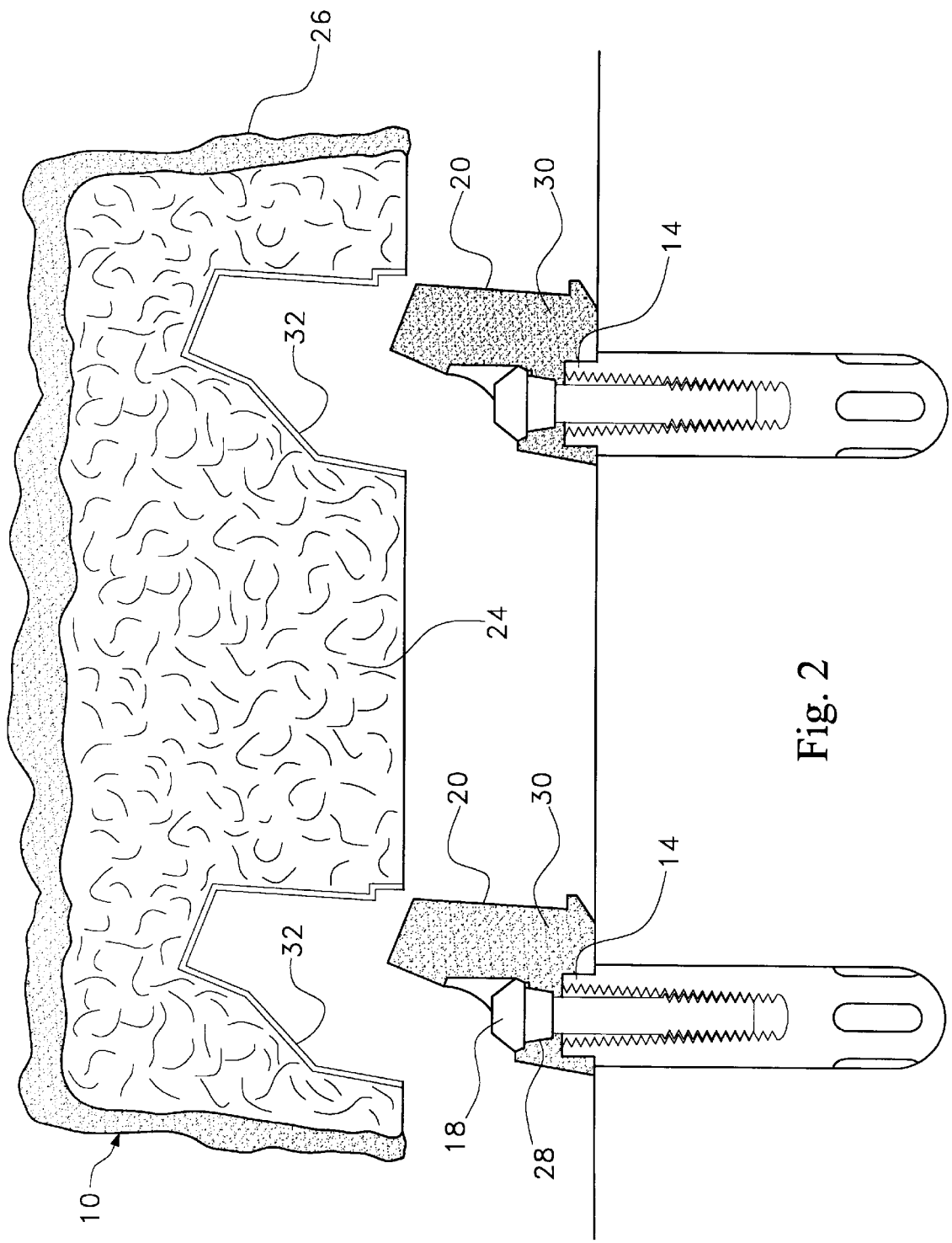
FIG. 2 is a cross-sectional view of the embodiment of the present invention shown in FIG. 1.

Once a model of the area of occlusion is fabricated, the bridge prosthesis 10 can be created. Referring to FIG. 2, it can be seen that the bridge prosthesis 10 is fabricated utilizing a fiber reinforced composite substructure 24 coated with a ceramic optimized polymer veneering material 26. The fiber reinforced composite substructure 24 contains preimpregnated glass fibers that are silanized to form a chemical bond with a polymer resin. The glass fibers are typically 5 μm to 14 μm in diameter. The fibers are both stabilized and strengthened by the copolymerization of the silane on the fibers with the polymer resin. The polymer resin used within the fiber reinforced composite substructure 24 is a light curable material. The matrix formed by the glass fibers and the polymer resin creates a dentin colored translucent structure which, when cured, mimics the color and translucency of natural teeth.

In the preferred embodiment, the polymer resin contained within the ceramic optimized polymer on the exterior of the abutments 20 is the same polymer resin as is contained within the fiber reinforced composite substructure 24. Since both structures contain the same material, they are chemically compatible and both structures will readily bond to one another.

An example of fiber reinforced composite material that contains the same polymer resin as the ceramic optimized polymer previously described is sold commercially under the brand name Vectris™. Vectris™ is manufactured by Ivoclar Williams of Amherst, N.Y.

Once the fiber reinforced composite substructure of the bridge is complete, the substructure is covered with a veneering material. The detail of the teeth is formed into the veneering material, using traditional modeling techniques. The preferred veneering material is the same ceramic optimized polymer that is used to coat the exterior of the abutment.

As mentioned, the abutment 20 in FIG. 2 is coated with a ceramic optimized polymer 30. The entire body can be made of the ceramic optimized polymer. However, in a preferred embodiment, each abutment 20 is made of a fiber reinforced composite that is coated with the ceramic optimized polymer. The polymer resin used in both the fiber reinforced composite and the ceramic optimized polymer are preferably the same. An optional metal washer 28 can be provided to disperse the forces applied by the mounting screw 18.

Each abutment 20 can be joined to the bridge prosthesis 10 in a number of ways. In the embodiment of FIG. 2, the abutment and/or the abutment cavity in the bridge prosthesis can be coated with a thin coat of the light curable polymer resin 32 that is used in the formation of both the abutment 20 and the fiber reinforced composite substructure 24 of the bridge prosthesis 10. The bridge prosthesis 10 is placed onto the abutments 20 and the light curable polymer resin 32 is cured with exposure to light that passes through the translucent material of the bridge prosthesis. The result is a translucent, metal-free bridge prosthesis that is directly attached to a dental implant fixture 14, via an abutment 20, that is fabricated from the same metal-free material as is the bridge prosthesis 10.

Figure 3:
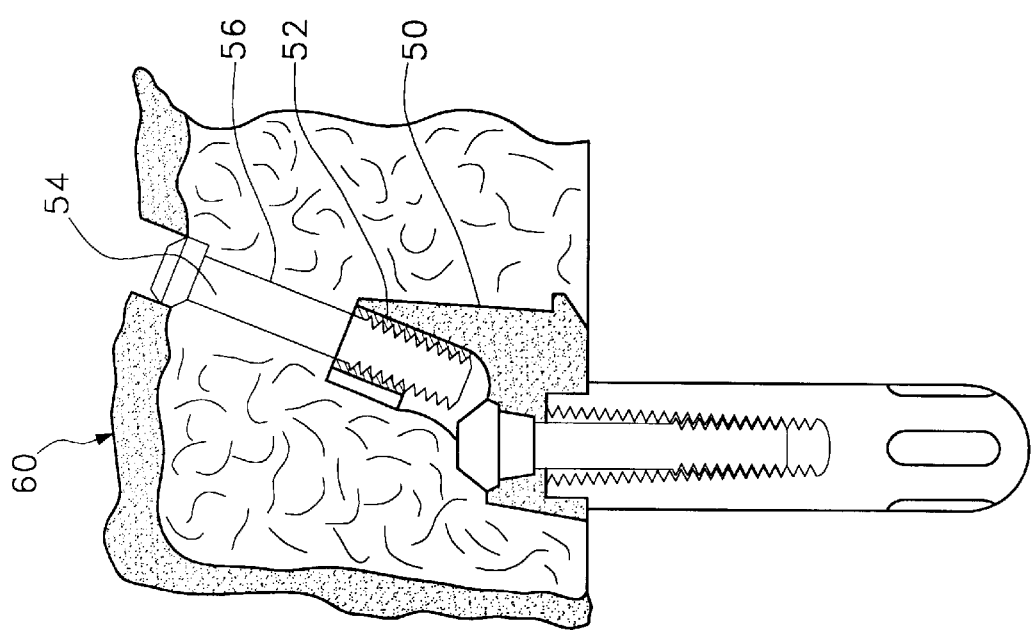
FIG. 3 is a cross-sectional view of an alternate embodiment of the present invention system.

Referring to FIG. 3, an alternative embodiment of the present invention system is shown. In this embodiment, the abutment 50 contains a threaded bore 52 lined with a metal bore thread sleeve 52. The threaded bore aligns with an aperture 56 in the structure of the bridge prosthesis 60. In all other aspects, the structure of both the abutment 50 and the bridge prosthesis 60 are the same as has been previously described. An attachment screw 54 passes through the bridge prosthesis 60 and engages the abutment 50, thereby creating a mechanical connection between the abutment 50 and the bridge prosthesis 60 that supplements and light cured adhesive bond that was previously described in reference to the embodiment of FIG. 2.

Figure 4:
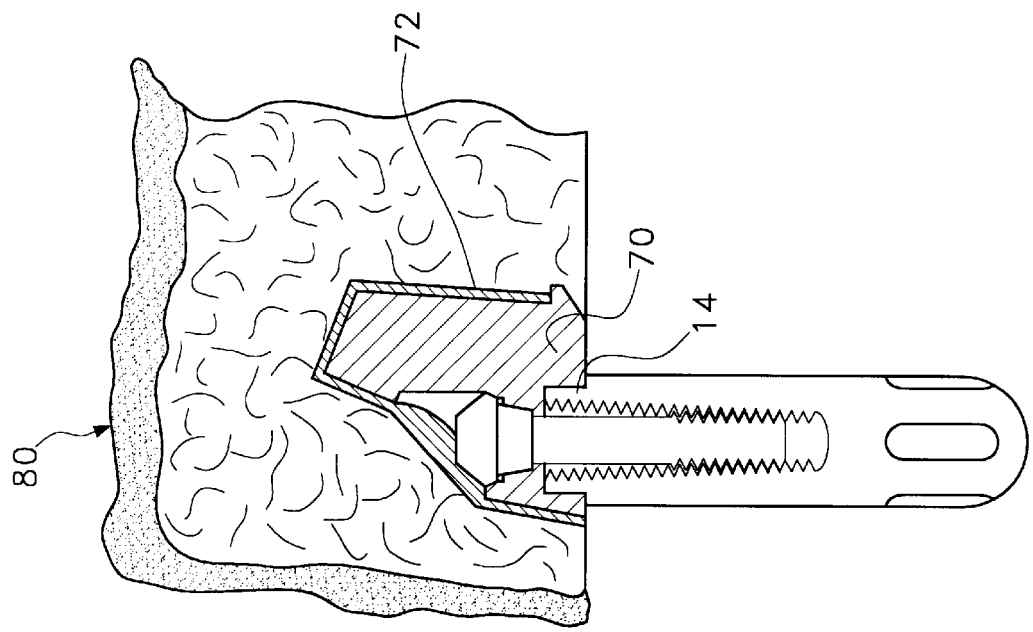
FIG. 4 is a cross-sectional view of a third embodiment of the present invention system.

Referring to FIG. 4, a third embodiment of the present invention system is shown. In this embodiment a standard prior art metal abutment 70 is attached to the dental implant fixture 14. The bridge prosthesis 80 is fabricated from metal free materials as has previously been described. Poor adhesion qualities are typically available between traditional abutment metals and fiber reinforced composites. As a result, even though the bridge prosthesis can be directly attached to the metal abutment with a screw, it is preferred that a metal cylinder 72 is placed over the abutment or under the bridge prosthesis. The metal cylinder 72 is preferably made of gold or another such metal that can be bonded to the fiber reinforced composite and is compatible with the metal of the abutment.

Figure 5:
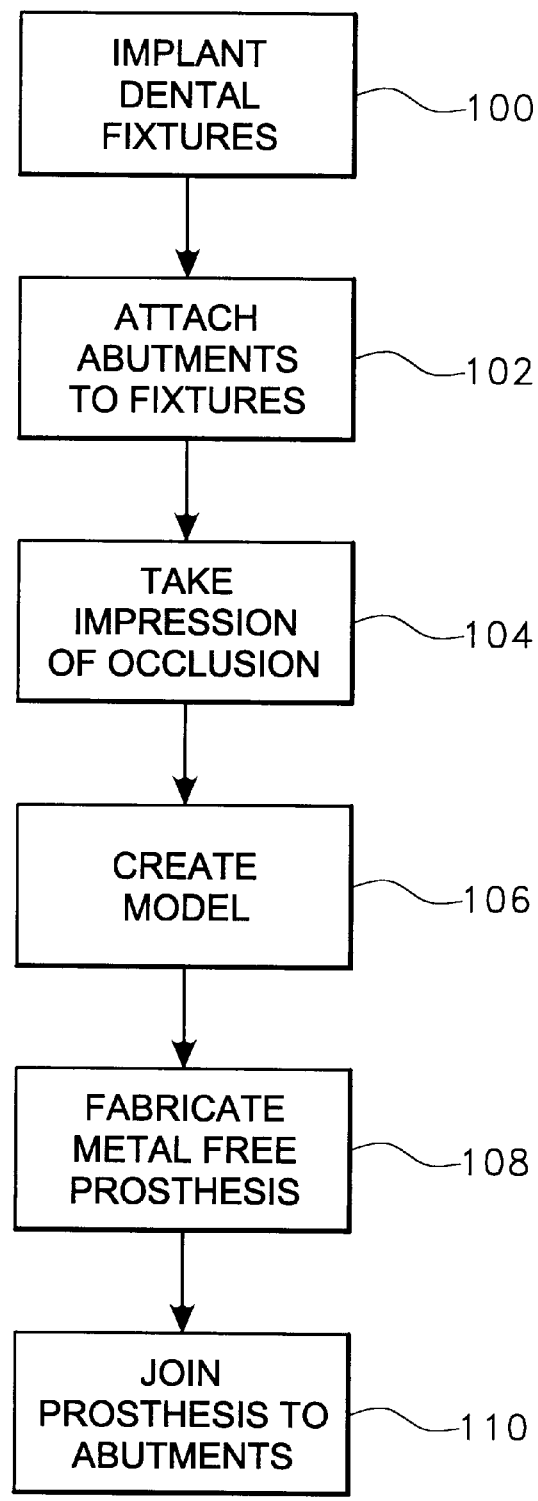
FIG. 5 is a method logic flow schematic illustrating a preferred method of filling a dental occlusion.

For the embodiments of FIGS. 2, 3 and 4, a common method of dental prosthesis fabrication is followed. Referring to FIG. 5, it can be seen from Block 100 that the first step in the method is to implant dental fixtures using traditional dental surgery techniques. After the dental implants have healed, abutments are attached to the fixtures, as is indicated by Block 102. An impression of the area of occlusion is taken using traditional impression modeling techniques. (See Block 104) The impression will contain the position and configurations of the abutments. The impression is used to create a model of the area of the occlusion containing the abutments, as shown by Block 106.

Referring to Block 108, the model is used to create a metal free prosthesis. The metal free prosthesis has a fiber reinforced composite substructure coated with a ceramic optimized polymer veneer. The metal free prosthesis is then joined to the abutments, in one of the manners previously described, as indicated by Block 110.

Once the metal free prosthesis is attached to the implant fixtures within the mouth, the dental prosthesis is firmly anchored without reliance upon existing adjacent teeth. The dental prosthesis is translucent and can be fabricated to have the appearance of a natural tooth. Should the dental prosthesis ever chip or crack, the dental prosthesis can be repaired intraorally. Light curable composite resin can be used in the mouth to make repairs of the dental prosthesis, thereby greatly increasing the life of the dental fixture before it requires replacement.

It will be understood that the embodiments of the present invention system and method described and illustrated herein are merely exemplary and a person skilled in the art can make many variations to the embodiment shown without departing from the scope of the present invention. All such variations, modifications and alternate embodiments are intended to be included within the scope of the present invention as defined by the appended claims.

What is claimed is:

1. A dental prosthesis system for filling a dental occlusion within the mouth, comprising:
   at least one dental implant fixture capable of being surgically implanted into the mouth within the occlusion;
   an abutment for each said dental implant fixture, wherein each said abutment is attachable to a dental implant fixture, and has an exterior surface fabricated from a material that contains a predetermined polymer matrix;
   a metal free prosthesis attachable to each said abutment, said metal free prosthesis having a substructure covered by a veneer that provides a translucency comparable to natural teeth, wherein said substructure contains glass fibers set within said predetermined polymer matrix, and said veneer is a ceramic optimized polymer containing ceramic filler particles embedded in said predetermined polymer matrix.

2. The system according to claim 1, wherein each said abutment has an exterior surface containing a ceramic optimized polymer.

3. The system according to claim 1, wherein said prosthesis is bonded to each said abutment with a light curable polymer.

4. The system according to claim 1, further including at least one screw for interconnecting said prosthesis to each said abutment.

5. The system according to claim 1, further including a metal cylinder disposed between each said abutment and said prosthesis.

6. A method of filling a dental occlusion with a metal free prosthesis, comprising the steps of:
   surgically implanting at least one dental implant fixture within the occlusion;
   providing an abutment having an external surface that contains a predetermined polymer matrix
   attaching an abutment to each said dental implant fixture;
   taking an impression of the area of the occlusion over any abutment;
   creating a dental model from said impression;
   fabricating a metal free prosthesis from said model by fabricating a substructure within said prosthesis from a fiber reinforced composite and veneering said substructure with a ceramic optimized polymer, wherein said fiber reinforced composite and said ceramic optimized polymer both contain said predetermined polymer matrix; and
   affixing said prosthesis to each abutment.

7. The method according to claim 6, wherein said step of affixing said prosthesis to each abutment includes placing a light curable material between said prosthesis and each abutment and curing said light curable material.

8. The method according to claim 6, wherein said step of affixing said prosthesis to each abutment includes driving a screw through said prosthesis into each abutment.

9. The method according to claim 6, further including the step of positioning a metal cylinder between said prosthesis and each said abutment, wherein said cylinder is bonded to both said prosthesis and said abutment.

* * * * *